US009005680B2

(12) United States Patent
Fetissova et al.

(10) Patent No.: US 9,005,680 B2
(45) Date of Patent: Apr. 14, 2015

(54) ORAL COMPOSITIONS COMPRISING PROPOLIS

(71) Applicant: Colgate-Palmolive Company, New York, NY (US)

(72) Inventors: Nataly Fetissova, Moscow (RU); Claude Blanvalet, Angleur (BE); Pierre Lambert, Bottmingen (CH)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/521,250

(22) Filed: Oct. 22, 2014

(65) Prior Publication Data

US 2015/0044266 A1   Feb. 12, 2015

Related U.S. Application Data

(63) Continuation of application No. 13/908,740, filed on Jun. 3, 2013, now abandoned, which is a continuation of application No. 11/611,701, filed on Dec. 15, 2006, now abandoned.

(60) Provisional application No. 60/752,617, filed on Dec. 21, 2005.

(51) Int. Cl.
| | |
|---|---|
| *A01N 65/00* | (2009.01) |
| *A61K 8/98* | (2006.01) |
| *A61K 8/33* | (2006.01) |
| *A61K 8/81* | (2006.01) |
| *A61K 8/21* | (2006.01) |
| *A61Q 11/00* | (2006.01) |

(52) U.S. Cl.
CPC . *A61K 8/988* (2013.01); *A61K 8/33* (2013.01); *A61K 8/8164* (2013.01); *A61K 8/21* (2013.01); *A61Q 11/00* (2013.01); *A61K 2800/592* (2013.01); *A61K 2800/48* (2013.01); *A61K 2800/42* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 4,894,220 A | 1/1990 | Nabi et al. |
| 5,037,635 A | 8/1991 | Nabi et al. |
| 5,156,835 A | 10/1992 | Nabi et al. |
| 5,288,480 A | 2/1994 | Gaffar et al. |
| 5,292,502 A | 3/1994 | Burke et al. |
| 5,344,641 A | 9/1994 | Gaffar et al. |
| 5,376,374 A | 12/1994 | Zelaya |
| 5,538,715 A | 7/1996 | Gaffar et al. |
| 5,776,435 A | 7/1998 | Gaffar et al. |
| 5,922,324 A | 7/1999 | Aga et al. |
| 6,149,894 A | 11/2000 | Yamane et al. |
| 6,153,227 A | 11/2000 | Shibuya et al. |
| 6,153,228 A | 11/2000 | Shibuya et al. |
| 6,162,449 A | 12/2000 | Maier et al. |
| 6,197,305 B1 | 3/2001 | Friedman et al. |
| 6,290,933 B1 | 9/2001 | Durga et al. |
| 6,369,217 B1 | 4/2002 | Maier et al. |
| 6,503,483 B2 | 1/2003 | Shuch et al. |
| 6,685,921 B2 | 2/2004 | Lawlor |
| 6,692,726 B1 | 2/2004 | Morgan et al. |
| 6,726,898 B2 | 4/2004 | Jernberg |
| 8,119,169 B2 | 2/2012 | Worrell et al. |
| 2003/0206874 A1 | 11/2003 | Doyle et al. |
| 2003/0215433 A1 | 11/2003 | Kokai-Kun et al. |
| 2003/0216481 A1 | 11/2003 | Jia |
| 2004/0057908 A1 | 3/2004 | Bowen et al. |
| 2004/0258631 A1 | 12/2004 | Boyd et al. |
| 2005/0058602 A1 | 3/2005 | Ramji et al. |
| 2006/0014088 A1 | 1/2006 | De Boer et al. |
| 2006/0120975 A1 | 6/2006 | Scherl et al. |
| 2006/0134015 A1 | 6/2006 | Trivedi et al. |
| 2006/0134025 A1 | 6/2006 | Trivedi et al. |
| 2006/0140881 A1 | 6/2006 | Xu et al. |
| 2006/0140885 A1 | 6/2006 | Gaffar et al. |
| 2006/0141073 A1 | 6/2006 | Worrell et al. |
| 2007/0014740 A1 | 1/2007 | Miller et al. |
| 2007/0140990 A1 | 6/2007 | Fetissova et al. |

FOREIGN PATENT DOCUMENTS

| | | |
|---|---|---|
| CA | 2006713 | 6/1990 |
| CA | 2006719 | 6/1990 |
| CA | 2046013 | 1/1992 |
| CA | 2060289 | 7/1992 |
| CN | 1171929 A | 2/1998 |
| CN | 1536989 A | 10/2004 |
| CN | 1634155 A | 7/2005 |
| DE | 20220964 | 9/2004 |
| EP | 0579333 | 1/1994 |
| EP | 1236466 | 9/2002 |

(Continued)

OTHER PUBLICATIONS

Avalon Organics, 2005, "Ingredient Glossary A-Z" www.avalonorganics.com website.
Baehni et al., 2003, "Anti-Plaque Agents in the Prevention of Biofilm-Associated Oral Diseases," Oral Diseases 9(Suppl. 1):23-29.
Barrett, 1999, "Bee Pollen, Royal Jelly & Propolis," www.quackwatch.com website.
Botushanov et al., 2001, "A Clinical Study of a Silicate Toothpaste with Extract from Propolis," Folia Medica 43(1-2):28-30.
Colgate-Palmolive Company, 2005, Total Plus Whitening Gel Toothpaste Packaging.

(Continued)

*Primary Examiner* — Michael Meller
(74) *Attorney, Agent, or Firm* — Anne Louise St. Martin

(57) ABSTRACT

Oral compositions are provided that comprise a propolis extract; a halogenated diphenyl ether non-ionic antibacterial agent; an anionic polymeric copolymer of methyl vinyl ether and maleic anhydride; and a source of fluoride ions. The oral composition can be in a form of a mouth rinse, a dentifrice, a confectionary, a medicament, or a film. Methods of making and using the oral compositions are also provided.

1 Claim, No Drawings

(56) References Cited

FOREIGN PATENT DOCUMENTS

| JP | H01-503142 | 10/1989 |
|---|---|---|
| JP | H06-65083 A | 3/1994 |
| JP | H11-255629 | 9/1999 |
| JP | 2005-29498 A | 2/2005 |
| JP | 2005-220087 A | 8/2005 |
| WO | WO 99/34811 | 7/1999 |
| WO | WO 02/02096 | 1/2002 |
| WO | WO 02/47615 | 6/2002 |

OTHER PUBLICATIONS

Dictionary Die, "Definition of Bee Glue," www.diet.die.net website accessed 2014.
Dorland's Medical Dictionary, "Definition of Adhesin," www.mercksource.com, retrieved from internet 2005.
Dorland's Medical Dictionary, "Definition of Adhesion," www.mercksource.com, retrieved from internet 2005.
Dorland's Medical Dictionary, "Definition of Glycoprotein," www.mercksource.com, retrieved from internet 2005.
Dorland's Medical Dictionary, "Definition of Glycosyltransferase," www.mercksource.com, retrieved from internet 2005.
Dorland's Medical Dictionary, "Definition of Gram negative and Gram positive," www.mercksource.com, retrieved from internet 2005.
Dorland's Medical Dictionary, "Definition of Ligand and Ligase," www.mercksource.com, retrieved from internet 2005.
Finlay-Jones et al., "Anti-Inflammatory Activity of Tea Tree Oil," Rural Industries Research & Development Corporation, www.rirde.gov.au/reports/TTO/01-I0sum.html website.
Hegazi, "Propolis An Overview," www.apinetla.com.ar/congreso/c05.pdf website retrieved form internet 2014.
International Search Report and Written Opinion in International Application No. PCT/US06/062502, mailed May 18, 2007.
Krell, 1996, "Chapter 5: Propolis," Value-Added Products for Bee-keeping www.fao.org website.
Melaleuca, 2005, "Whitening Tooth Polish." Database Mintel GNPD No. 10208461.
Navarre et al., 1999, "Surface Proteins of Gram-Positive Bacteria and Mechanisms of Their Targeting to the Cell Wall Envelope," Microbiol. Mol. Biol. Rev. 63(1):174-229.
Orsolic et al., 2005, "Peroral application of water-soluble derivative of propolis (WSDP) and its related polyphenolic compounds and their influence on immunological and antitumour activity," Vet. Res. Commun. 29(7):575-593.
Ray et al., 1999, "Interactions of *Streptococcus mutans* Fimbria-Associated Surface Proteins with Salivary Components," Clinical Diagn. Lab. Immunol. 8(3):400-404.
Santos et al., 2005, "Oral candidiasis treatment with Brazilian ethanol propolis extract," Phytother. Res. 19(7):652-654.
Todar, 2002, "Mechanisms of Bacterial Pathogenicity: Endotoxins," Todar's Online Textbook of Bacteriology www.textbookofbacteriology.net/endotoxin website.
Todar, 2002, "The Bacterial Flora of Humans," Todar's Online Textbook of Bacteriology www.textbookofbacteriology.net/normalflora.html website.
WordIQ, 2010, "Definition of Apidae," www.wordiq.com/definition/Apidae website.
WordIQ, 2010, "Definition of *Apis* (genus)," www.wordiq.com/definition.Apis_%28genus%29 website, retrieved from internet 2014.
WordIQ, 2010, "Definition of *Apis mellifera caucasica*," www.wordiq.com/definition/Apis_mellifera_caucasica website.
WordIQ, 2010, "Definition of Apoidea," www.wordiq.com/definition/Apoidea website.
WordIQ, 2010, "Definition of Propolis" www.wordiq.com/definition/Propolis.

ORAL COMPOSITIONS COMPRISING PROPOLIS

CROSS REFERENCE TO RELATED APPLICATION

This application is a continuation of U.S. application Ser. No. 13/908,740 filed Jun. 3, 2013, which is a continuation of U.S. application Ser. No. 11/611,701 filed Dec. 15, 2006, which claims benefit of U.S. Provisional Patent Application No. 60/752,617 filed Dec. 21, 2005, which is incorporated herein by reference in its entirety.

BACKGROUND OF THE INVENTION

Human periodontal diseases are inflammatory disorders that are the result of complex interactions between periodontopathogens and the host's immune system response. It is believed that there are two interrelated aspects to the progression of periodontal disease; the first is the activation of the immune system of the host and the second is the production of oxygen radicals and their related metabolites. Increased production of oxygen radicals may contribute to oxidative stress, which is believed to be involved in periodontal disease.

Gingivitis is the inflammation or infection of the gums and the alveolar bones that support the teeth. Gingivitis is generally believed to be caused by bacteria in the mouth (particularly the bacteria associated with plaque formation) and the inflammatory response triggered by the presence of bacteria and the toxins formed as by-products from the bacteria. Periodontitis is a progressively worsened state of disease as compared to gingivitis, where inflamed gums begin to recede from the teeth, thus forming pockets there between, which can ultimately result in destruction of the bone and periodontal ligament. Chronic infection and inflammation potentially results in the subsequent loss of teeth.

It is generally believed that the cellular components implicated by these diseases and conditions include epithelial tissue, gingival fibroblasts, and circulating leukocytes, all of which contribute to the host response to pathogenic factors generated by the bacteria. Although the bacterial infection is often the etiological event in many of these oral diseases, the pathogenesis of the disease is mediated by the host response.

Bacterial infection of the oral tissue increases the host's immune system response and diminishes the healing process by up-regulating inflammatory mediators that can induce significant tissue damage surrounding the foci of infection.

There is a need for oral care compositions that effectively reduce the development or progression of oral disease, preferably by having an active ingredient that diminishes the effects of oral disease by preventing or reducing multiple etiological factors that contribute to and/or exacerbate oral disease. Further, there is a need to stabilize oral care actives in an oral composition, so that their functionality and bioavailability as delivered to a subject in vivo is preserved and stabilized.

BRIEF SUMMARY OF THE INVENTION

In certain embodiments, the present invention is directed to an oral composition comprising:
 a propolis extract;
 an oral care active compound chosen from: a cationic antibacterial agent, an anti-attachment agent, a biofilm disruption agent or an anti-inflammatory agent; and
 a source of fluoride ions.

In certain embodiments, the present invention is directed to a method of making an oral composition comprising:
 admixing one or more carrier ingredients to form a homogenous mixture;
 adding a fluoride ion source to the mixture;
 adding at least one of: a cationic antibacterial agent, an anti-attachment agent, a biofilm disruption agent or an anti-inflammatory agent; and
 adding a propolis extract to the homogeneous mixture at temperatures of less than or equal to about 40° C. to form the oral composition.

In certain embodiments, the present invention is directed to methods of preventing bacterial from forming a biofilm, suppressing an immune system recognition of an antigen on an oral surface of a mammal, reducing an immune system response, and suppressing production of one or more mediators of inflammation on an oral surface, comprising administering and applying the compositions herein to the oral surface. In certain embodiments, the present invention is directed to methods of maintaining or increasing systemic health of a mammal comprising applying a composition according to claim to the oral surfaces at least once a day a period of time.

DETAILED DESCRIPTION OF THE INVENTION

As referred to herein, all references cited herein are hereby incorporated by reference in their entireties. Where there is a conflict between a definition in the present disclosure and that of a cited reference, the present disclosure controls. Furthermore, all percentages expressed are weight percentages.

In various embodiments, an oral composition is provided that comprises an extract of propolis, and an oral care active compound chosen from: a cationic antibacterial agent, an anti-attachment agent, a biofilm disruption agent, an anti-inflammatory agent, or mixtures thereof. In some embodiments, the active ingredient may comprise three or more constituents. For example, in certain embodiments the active ingredient comprises a third constituent that comprises a source of fluoride ions. In other embodiments, the oral composition comprises an anionic polymeric linear polycarboxylate, as will be described in more detail below.

The compositions of the present invention comprise a propolis extract. As referred to herein, the terms "propolis," "propolis extract" or an "extract of propolis" refer to a composition that is obtained from a source produced by bees, which are generally classified in the family Apidae, preferably of the genus *Apis*. For example, suitable extracts include those isolated from a source generated by *Apis melifera* (commonly known as the "honeybee"), including its various sub-species (*Apis mellifera* ssp.), such as *Apis mellifera caucasica* (the "Caucasian honeybee" or the "western honeybee"). As referred to hereinafter, the terms "propolis," "propolis extract" or an "extract of propolis" encompass all suitable resin products produced by species and sub-species of the family Apidae, as well as synthetic or semi-synthetic equivalents of such natural extracts or active components contained therein.

It is reported that propolis contains numerous active compounds, including many classes of polyphenolic compounds, flavones, flavonones, phenolic acid, and esters. While these compounds are not entirely understood or characterized, they are generally believed to vary based upon the geographical location and where the bees are located. Generally, on a weight basis propolis contains about 45 to about 55% resins and balsams (including for example, flavonoids, phenolic acids, and esters); about 25 to about 35% waxes and fatty acids; about 10% essential oils; about 5% pollen (including proteins and protein-derived amino acids); and about 5% of other organic compounds and minerals (including trace minerals, vitamins, ketones, lactones, quinones, steroids, benzoic acid and esters, and sugars); among other compounds.

In certain embodiments, the propolis extract comprises one or more active compounds that have been isolated from a propolis source. The propolis extract may include a complement of active compounds naturally occurring in the propolis source. A propolis extract of the present invention may include a form of the extract and at least one active compound, for example two or more active compounds, or even a plurality of active compounds derived from a propolis source. In certain embodiments, various propolis extracts can be provided in hydrophilic or lipophilic carriers, depending on the solvent used during extraction. The extracts may be in a liquid, paste, or dried powder form.

Certain microorganisms are known to accumulate and promote formation of a dental plaque matrix (i.e., biofilm) on an oral surface, which in turn facilitates formation of tartar, gingivitis, periodontitis, caries, candidiasis, and/or denture stomatitis, inter alia. In certain embodiments, the compositions of the present invention inhibit the accumulation of such microorganisms. Propolis has been reported to inhibit the accumulation of microorganisms such as lactobacilli, *actinomyces*, leptotrichiae, non-β-hemolytic streptococci, enterococci, miscellaneous gram-positive cocci, neisseriae, diphtheroid bacilli, fusiform bacilli, *bacteroides*, spirochetes, yeasts (*Candida*), and combinations thereof. In accordance with various embodiments, the propolis extract may provide one or more of the following oral care benefits: antibacterial, anti-microbial, anti-inflammatory, anti-oxidant, anti-caries, antiplaque and anti-tartar.

As used herein, "extracting" or "extraction" of a solid or liquid material refers to contacting the material with an appropriate solvent to remove the substance(s) desired to be extracted from the material. Where the material is solid, it is preferably cleaned of debris and excess wax, and then broken into small pieces, crushed, or ground to a powder prior to contacting it with the solvent. Such an extraction may be carried out by conventional means known to one of skill in the art; for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting. It is preferred that natural extract active ingredients used in oral care compositions are of reproducible, stable quality and have microbiological safety.

Propolis extract may be prepared by extracting the solid propolis material using an appropriate solvent. Selection of the extraction solvent is typically dictated by the final use of the extract and on technical feasibility. Preferred non-limiting solvents for extraction include monohydric solvents, i.e., alcohols such as methanol, and ethanol; polyhydric solvents, such as propylene glycol; acetic acid; sodium hydroxide (preferably in combination with water); water; oils; and the like. While other solvents can also be used for extraction of propolis, such as ether, acetone, benzene and ammonia, they are generally not considered suitable for use in oral care compositions.

Other methods of extraction include steam distillation or supercritical fluid extraction. In one embodiment, the propolis extract is isolated by supercritical fluid extraction (SFE), such as SFE using carbon dioxide ($CO_2$), steam distillation or using vehicles such as sunflower or avocado oils. Methods of preparing a propolis extract can include those known in the art, such as, for example, those described in U.S. Pat. Nos. 6,153,227 and 6,153,228 to Shibuya et al. and U.S. Pat. No. 5,922,324 to Aga et al.

Generally, one part of propolis (dry basis) is extracted with about 1 to about 50 parts of solvent, preferably from about 10 parts to about 40 parts of solvent using an extraction apparatus where the solvent is contacted with the propolis matter to obtain a concentrated extract. The extract can be in the form of a paste, which is then optionally subjected to one or more additional extraction steps with different solvents to further concentrate the originally obtained paste over an extended period of time, for example about 6 hours to about 2 days, or for about 1 day. The propolis may be extracted with a mixture of a polyhydric compound and water. For example, the extraction solvent may be a mixture of water to propylene glycol, in a ratio of about 1:2 to about 2:1. In certain embodiments, the first constituent comprising propolis extract comprises one or more active compounds derived from a propolis source, at from about 1 to about 75% by weight of the extract. In certain embodiments, the propolis extract product is in a liquid form. Thus, the first constituent comprises about 1 to about 5% by weight of active compounds derived from the propolis source, about 94 to about 99% solvent and optionally about 0.1 to about 1% other compounds, such as preservatives and impurities.

In various embodiments, the propolis extract is present in the oral composition of about 0.0001 to about 3% by weight, less than about 1% by weight, about 0.0002 to about 1% by weight or about 0.0003 to about 0.5% by weight.

As described above, the oral compositions of the present invention further comprise an oral care active compound chosen from: a cationic antibacterial agent, an anti-attachment agent, a biofilm disruption agent, an anti-inflammatory agent, or mixtures thereof. As appreciated by one of skill in the art, an oral care active compound may fall into one or more of these classifications, as it may have multiple mechanisms and/or effects, and may not be limited to a single function or classification. In certain embodiments, the oral care active compound has a functionality or mechanism for preventing and/or treating an oral care disease, where the mechanism complements and/or supplements the mechanism provided by the propolis extract described above. In addition, for the present purposes, the terms "cationic antibacterial agent," "anti-attachment agent," "biofilm disruption agent" and "anti-inflammatory agent" refer to compositions other than propolis extracts.

In certain embodiments, the oral care active compound is a cationic antibacterial agent that is highly effective in oral care compositions for use in certain embodiments. Suitable cationic antibacterial agents for use in oral compositions include, for example:

(i) quaternary ammonium compounds, such as those in which one or two of the substituents on the quaternary nitrogen has from 8 to 20, preferably from 10 to 18 carbon atoms and is preferably an alkyl group, which may optionally be interrupted by an amide, ester, oxygen, sulfur, or heterocyclic ring, while the remaining substituents have a lower number of carbon atoms, for instance from 1 to 7, and are preferably alkyl, for instance methyl or ethyl, or benzyl. Examples of such compounds include benzalkonium chloride, dodecyl trimethyl ammonium chloride, benzyl dimethyl stearyl ammonium chloride, hexadecyltrimethyl ammonium bromide, benzethonium chloride (diisobutyl phenoxyethoxyethyl dimethyl benzyl ammonium chloride) and methyl benzethonium chloride;

(ii) pyridinium and isoquinolinium compounds, including hexadecylpyridinium chloride and alkyl isoquinolinium bromides;

(iii) pyrimidine derivatives such as hexetidine (5-amino-1, 3-bis(2-ethylhexyl)-5-methyl-hexahydropyrimidine);

(iv) amidine derivatives such as hexamidine isethionate (4,4'-diamidino-αω-diphenoxy-hexane isethionate);

(v) bispyridine derivatives such as octenidine dihydrochloride (N,N'[1,10-decanediyldi-1(4H)-pyridinyl-4-ylidene]-bis(1-octanamine) dihydrochloride);

(vi) guanides, for example, mono-biguanides such as p-chlorobenzyl-biguanide and N'(4-chlorobenzyl)-N"-(2,4-dichlorobenzyl) biguanide, poly(biguanides) such as polyhexamethylene biguanide hydrochloride, and bis-biguanides of the general formula (1):

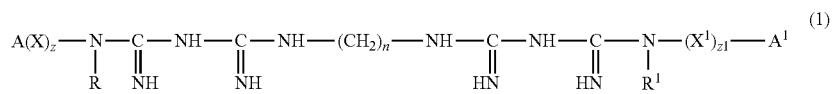

in which A and $A^1$ each represent (i) a phenyl group optionally substituted by $(C_{1-4})$ alkyl, $(C_{1-4})$ alkoxy, nitro, or halogen, (ii) a $(C_{1-12})$ alkyl group, or (iii) a $(C_{4-12})$ acyclic group; X and $X^1$ each represent $(C_{1-3})$ alkylene; R and $R^1$ each represent hydrogen, $(C_{1-12})$ alkyl, or aryl $(C_{1-6})$ alkyl; Z and Z1 are each 0 or 1; n is an integer from 2 to 12; and the polymethylene chain $(CH_2)_n$ may optionally be interrupted by oxygen or sulfur or an aromatic (for instance, phenyl or naphthyl) nucleus; and orally acceptable acid addition salts thereof; examples of such bis-biguanides include chlorhexidine and alexidine. Suitable acid addition salts of the bis-biguanides of general formula (1) include the diacetate, the dihydrochloride and the digluconate. Suitable acid addition salts of chlorhexidine include the digluconate, diformate, diacetate, dipropionate, dihydrochloride, dihydroiodide, dilactate, dinitrate, sulphate, and tartrate salts. Suitable acid addition salts of alexidine include the dihydrofluoride and the dihydrochloride salts; and (vii) $N^\alpha$-acyl amino acid alkyl esters and salts generally represented by the formula (2) below:

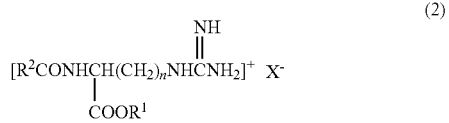

where $R^1$ is an alkyl chain of 1 to 8 carbon atoms, preferably from 1 to 3 carbon atoms, and most preferably 3 carbon atoms; $R^2$ is an alkyl chain of 6 to 30 carbon atoms, preferably from 10 to 12 carbon atoms, and mixtures thereof; and X is an anion. In various embodiments, the $R^2CO$ moiety comprises a natural fatty acid residue such as a natural fatty acid chosen from coconut oil fatty acid, tallow fatty acid residue, or a mono-fatty acid residue such as lauroyl $(C_{12})$, myristyl $(C_{14})$, stearoyl $(C_{18})$ fatty acid residues, or mixtures thereof. In certain embodiments, the $R^2CO$ moiety comprises a lauroyl fatty acid residue.

X may be any counter-anion that provides a reasonable degree of solubility in water (preferably at least about 1 g in 1 L of water). Examples of X counter anions that form antibacterial ester salts of the above identified formula, include inorganic acid salts, such as those comprising halogen atoms (e.g., chloride or bromide) or dihydrogen phosphate, or an organic salt such as acetate, tautarate, citrate, or pyrrolidone-carboxylate (PCA).

Examples of useful antibacterial esters of the above-identified formula wherein n equals 3 include: N'-cocoyl-L-arginine methyl ester, $N^\alpha$-cocoyl-L-arginine ethyl ester, $N^\alpha$-cocoyl-L-arginine propyl ester, $N^\alpha$-stearoyl-L-arginine methyl ester, $N^\alpha$-stearoyl-L-arginine ethyl ester hydrochloride. In one embodiment, the arginine derivative compound is the hydrogen chloride salt of ethyl lauroyl arginine (ELAH). It should be noted that the $N^\alpha$-acyl amino acid alkyl ester salts are generally classified as cationic antibacterial agents. However, such compounds also tend to exhibit anti-attachment and other properties that prevent the formation of plaque on oral surfaces, which will be described in more detail below.

Thus, in certain embodiments, the cationic antibacterial agent is chosen from: benzethonium chloride, octenidine, hexetidine, hexamidine, cetyl pyridinium chloride (CPC), alexidine, $N^\alpha$-acyl amino acid alkyl ester salts (such as ethyl lauroyl arginine ester hydrochloride (ELAH)), and mixtures thereof.

In various embodiments, the cationic antibacterial agent is present in the oral compositions in an amount of about 0.001 to about 3%, about 0.005 to about 2% and about 0.01 to about 1%.

In other embodiments, the oral care active compound is an anti-attachment agent. While not limiting as to the present invention, oral care active compounds are generally believed to operate by either (or both) of two predominant anti-attachment mechanisms. Biofilms (also referred to as pellicle) are a matrix formed on an oral surface, typically on a hard tissue surface, comprising bacteria (generally about 60-70% of the biomatrix), bacterial extracellular byproducts, proteins, lipids, and glycolipids. The term "oral surface" encompasses hard and soft tissues within the oral cavity. Hard tissues include the teeth, periodontal support, and the like. Soft tissues comprise gums, the tongue, surfaces of the buccal cavity and the like. The oral compositions of the various embodiments can be used in a mammalian subject, which includes, inter alia, humans and other warm blooded higher level vertebrate animals, such as felines and canines.

Early stages of biofilm formation include an initial bacteria layer that attaches to an oral surface, generally believed to be attached by ligands or adhesins on the bacterial cell wall that interact with receptors on an oral surface. It is believed that the bacterial cells attach to the salivary glycoproteins on the oral surface, e.g., enamel. The bacteria appear to form a stronger attachment by generating extracellular glucan polymers to adhere to the oral surface. The bacteria then grow and divide, forming a dense layer on the oral surface. After a specific density is reached, it is believed that the bacteria reorganize and begin to form pillars and irregular surface structures. Further, the biofilm matrix is believed to have a complex association of multi-layered and diverse species that form cell clusters attached to the anchoring bacteria of the first layer.

Thus, anti-attachment agents can interact with an oral surface to form a protective layer, such that the bacteria and biofilm components cannot adhere to the oral surface, thereby preventing an initial anchoring layer from forming on the oral surface. Such an anti-attachment agent may substantially cover an oral surface, and prevent attachment of the bacteria and other components of the biofilm matrix. In a second mechanism of anti-attachment agents, the anti-attachment agent interacts with the bacteria itself to disable it from attaching to the oral surface, likely by interacting with the adhesins, ligands, or other moieties on the surface of the bacteria that would ordinarily facilitate a linkage with a receptor or other moiety at the oral surface. For example, certain active ingredients may interfere with a glucosyl transferase enzyme on bacterial outer cell walls, thereby preventing conversion of various sugars to glucans that would otherwise form the extracellular anchoring matrix for the biofilm.

While not limiting as to the present invention, it is believed that in some embodiments where the oral care active compound is selected to comprise an $N^\alpha$-acyl amino acid alkyl ester salts, such as ethyl lauroyl arginate hydrochloride (ELAH), the active ingredients function as an anti-attachment active ingredient, in addition to a cationic antimicrobial ingredient. ELAH appears to alter the surface energy of hard tissues, such as enamel (by reducing the surface energy), and in turn, prevents adherence and attachment of microorganisms that may otherwise form a plaque biofilm on the tooth surface. ELAH appears to have substantivity on the tooth surface, such that it remains attached for a sufficient period of time to effectively prevent microorganisms from adhering to the tooth surface, thereby preventing or reducing biofilm formation.

In various embodiments, such an anti-attachment effect may be obtained at low concentrations, potentially below the Minimum Inhibitory Concentration (MIC) for ELAH. In various embodiments, the application of the ELAH as an active ingredient promotes longer and more effective anti-plaque benefits at lower concentrations in comparison with many other antimicrobial ingredients that are washed away in the aqueous oral cavity. Further, without limiting the present invention, it is hypothesized that ELAH may interfere with the metabolism of microorganisms in the biofilm, perhaps by arginine regulation, and in this manner contribute to the antimicrobial, anti-plaque, anti-gingivitis, and anti-periodontitis efficacy of the active ingredient in oral compositions (thus also performing as a biofilm disruption agent).

In various embodiments, the anti-attachment agent is present in the oral compositions in an amount of about 0.001 to about 3%, about 0.005 to about 2% and about 0.01 to about 1%.

In some embodiments, the oral care active compound is a biofilm disruption agent. A biofilm disruption agent is a compound that prevents formation of and/or attacks a biofilm already formed on an oral surface.

Enzymes have conventionally been selected as biofilm disruption agents, based upon the ability of various enzymes to hydrolyze proteins, starch and lipids, which form a part of a biofilm matrix. In certain embodiments, such enzymes include protease enzymes, such as cysteine proteases. In certain embodiments, the biofilm disruption agent is an enzyme chosen from: papain, ficin, krillase or mixtures thereof.

Papain is obtained from the latex of the green fruit and leaves of *Carica papaya*. Papain hydrolyzes polypeptides, more specifically, cleaving the carboxy terminus of arginine, lysine, glutamine, tyrosine, glycine, histidine (adjacent to phenylalanine) yielding peptides of lower molecular weight. Ficin is obtained by drying and filtering the latex from the *Ficus* species (tropical fig trees *Ficus glabrata*). Krillase is extracted from Antarctic krill (*Euphausia superba*). It consists of endo- and exo-peptidases, which include four serine proteases and four carboxyopeptidases.

Other enzymes are also suitable for inclusion in oral compositions as plaque disruption agents. One selected enzyme that may be formulated in combination with a protease enzyme is the aforesaid glucoamylase. Glucoamylase is a saccharifying glucoamylase of *Aspergillus niger* origin cultivated by fermentation. This enzyme can hydrolyze both the $\alpha$-D-1,6 glucosidic branch points and the $\alpha$-1,4 glucosidic bonds of glucosyl oligosaccharides. Additional useful are $\alpha$ and $\beta$-amylase, dextranase and mutanase.

Other suitable enzymes for use as a plaque disruption oral care active compound include lysozyme, derived from egg white. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine. In vivo, these two carbohydrates are polymerized to form the cell wall polysaccharide. Additionally, pectinase, an enzyme that is present in most plants, may facilitate the hydrolysis of the polysaccharide pectin into sugars and galacturonic acid, thus contributing to degradation of bacteria and other microorganisms.

Other useful enzymes include lipases such as plant lipase, gastric lipase, pancreatic lipase, tannase lysozyme, serine proteases, bromelain, chymotrypsin, alcalase, amalysecs, lactoferrin, gingipains, glucose oxidase, elastases and/or cellusases. Other exemplary oral care biofilm disruption agents include synthetic histatin, furanone, and derivatives and mixtures of any of the above.

In various embodiments, the biofilm disruption agent is present in the oral compositions in an amount of about 0.001 to about 3%, about 0.005 to about 2% and about 0.01 to about 1%.

In certain embodiments, the oral care active compound is an anti-inflammatory agent. Suitable anti-inflammatory agents include cytokines and prostaglandins. The suppression of one or more of the above described proinflammatory mediators prevents and/or treats tissue damage and/or tissue loss when the tissue is inflamed. Thus, oral care active compounds that serve as anti-inflammatory agents to suppress one or more mediators of inflammation are useful for oral compositions.

Exemplary useful anti-inflammatory agents can include those that prevent the accumulation of inflammatory mediators derived from arachidonic acid pathway that is triggered by immune system detection of an antigen. One class of mediators that modulate for inflammatory response are arachidonic acid metabolites, namely prostaglandins, leukotrienes, and thromboxanes, which are produced through the cyclooxygenase or lipoxygenase enzyme pathways. These metabolites have been implicated as the prime mediators in gingivitis, periodontitis, osteomyelitis and other inflammatory diseases. For example, such anti-inflammatory agents that prevent the accumulation of inflammatory mediators from the arachidonic acid pathway, include non-steroidal anti-inflammatory drugs (NSAIDs). Examples of useful NSAID anti-inflammatory agents include indomethicin, flurbiprofen, ketoprofen, ibuprofen, naproxen, meclofenamic acid or mixtures thereof.

In certain embodiments, the anti-inflammatory agent is capable of suppressing immune system recognition of one or more antigens produced by pathogens on an oral surface. For example, gram-negative bacteria have endotoxins, generally known as lipopolysaccharide (LPS) components, which are embedded within the outer membrane of the cell wall. The LPS of the bacterial cells serve as antigens that are detected by various cells within the immune system. The recognition of the LPS antigens by immune system cells, such as by CD-14 receptors on monocytes and macrophages, will typically result in an immune system response that includes production of cytokines, activation of the cascade complement (e.g., histamine release resulting in vasodilation and neutrophil chemotaxis), and activation of the coagulation cascade. Certain useful anti-inflammatory compounds may prevent an immune system from recognizing of one or more antigens present in the oral cavity, such as LPS on the cell walls of gram-negative bacteria. Such anti-inflammatory drugs are believed to interface with antigen in such a manner that the microbe/bacteria is no longer recognized by the receptors of certain cells of the immune system (effectively cloaking it from immune system detection) and thereby suppressing an immune system response.

Likewise, in another mechanism for oral care anti-inflammatory agents, the anti-inflammatory agent serves to reduce or scavenge one or more reactive oxide species within the oral cavity. Reactive oxygen species (ROS) are typically highly reactive products produced during various biochemical processes, and include superoxide anions ($O_2^-$), hydrogen peroxide ($H_2O_2$), and hydroxyl radicals (.OH). The formation of ROS can occur as part of many cellular processes including mitochondrial respiration, immune cell responses, cell injury, heat, radiation of many origins, from metabolism of drugs and other chemicals. ROS are thought to be involved in almost all disease processes, as well as in the ageing process. Increased ROS formation under pathological conditions is believed to cause cellular damage through the action of these highly reactive molecules by crosslinking proteins, mutagenizing DNA, and peroxidizing lipids.

Examples of active oral compounds that are anti-inflammatory agents that serve to reduce one or more ROS in the oral cavity, include oral care active compounds comprising at least one flavonoid compound. Flavonoids are generally described in are a class of compounds generally found in plants that have the same general structure and include compounds as flavones, flavans, flavonols, dihydroflanonols, flavonones, and derivatives thereof. In certain embodiments, the oral care anti-inflammatory agents comprise free-B-ring flavonoid compounds and/or flavans, which include flavanols. Compositions comprising free-B-ring flavonoids have been shown to inhibit activity of the cyclooxygenase enzyme COX-2, for example. Examples of suitable anti-inflammatory agents include those extracts and compounds derived from *Scutellaria baicalensis*, which contains significant amounts of free-B-ring flavonoids, including baicalein, baicalin, wogonin, and baicalenoside. A description of useful oral care anti-inflammatory agents comprising free-B-ring flavonoids may be found in U.S. Patent Application 60/639,329 to Trivedi et al. filed Dec. 22, 2004.

Certain oral care active ingredient anti-inflammatory agents include a mixture of at least one free-B-ring flavonoid and at least one flavan. Exemplary sources of flavans can be found in extracts derived from plants of the family Fabaceae, the subfamily Mimosoide, the genus *Acacia*. For example, suitable flavans can be isolated from the plant *Acacia catechu*. Catechin is an example of a flavan that is found extensively in *Acacia*, that exhibits, both alone and in conjunction with flavonoids, antiviral and antioxidant activity, as well as an ability to inhibit activity of both the COX-1 and COX-2 enzymes. A mixture of at least one free-B-ring flavonoid and a flavan is also suitable for use as an anti-inflammatory agent. A description of useful oral care anti-inflammatory agents comprising free-B-ring flavonoids and at least one flavan is found in U.S. Patent Application 60/639,331 to Xu et al. filed Dec. 22, 2004.

A commercially available oral care active comprising at least one free-B-ring flavonoid and at least one flavan is UNIVESTIN®, which is isolated from plants of the genus *Scutelleria*, and manufactured by Unigen Pharmaceuticals, Inc. (Superior, Colo., USA). A description of UNIVESTIN® can be found in, for example, U.S. Patent Application Publication 2003/0216481 to Jia. UNIVESTIN® inhibits specific enzymes that catalyze oral inflammatory pathways, such as and for example, the COX-1, COX-2, and 5-LO enzymes.

Another suitable anti-inflammatory agent is oregano extract. As referred to hereinafter, "oregano" encompasses all suitable species and sub-species of the genus *Origanum*; for example, *Origanum vulgare* (commonly known as "oregano,", "wild oregano" or "wild marjoram"), including its sub-species (*Origanum vulgare* ssp.), *Origanum onites* (commonly known as "Italian oregano" or "pot marjoram"), *Origanum majorana* (commonly known as "marjoram" or "sweet marjoram") and *Origanum heracleoticum*. *Origanum vulgare* subspecies include *O. vulgare* ssp. *vulgare*, *O. vulgare* ssp. *viride*, and *O. vulgare* ssp. *hirtum* (commonly known as "Greek oregano" or "Wild oregano"). Useful oral care active ingredients comprising oregano extract are discussed in U.S. patent application Ser. No. 11/256,788, Worrell et al. filed Oct. 24, 2005. Yet another suitable anti-inflammatory agent is *magnolia* extract, derived from plants in the Magnoliaceae family, such as *Magnolia officinalis*, that typically contains magnolol, honokiol, tetrahydromagnolol, and tetrahydrohonokiol, as described in U.S. Patent Application 60/640,161 to Gaffar et al. filed Dec. 29, 2004.

In various embodiments, the anti-inflammatory agent is present in the oral compositions in an amount of about 0.001 to about 3%, about 0.005 to about 2% and about 0.01 to about 1%.

In certain embodiments, a composition of the present invention further comprises a source of fluoride ions or fluorine-providing component, as anti-caries and/or anti-tartar agents, in an amount sufficient to supply about 25 ppm to about 5,000 ppm of fluoride ions. Examples of useful fluoride ion sources include inorganic fluoride salts, such as soluble alkali metal salts. For example, in certain embodiments, the fluoride source in the composition may be sodium fluoride, potassium fluoride, sodium monofluorophosphate, sodium fluorosilicate, ammonium fluoro silicate, amine fluorides, including olaflur (N'-octadecyltrimethylenediamine-N,N,N'-tris(2-ethanol)-dihydrofluoride), as well as tin fluorides, such as stannous fluoride.

Synthetic anionic linear polycarboxylates are efficacy enhancing agents for optional use in oral compositions having certain active ingredients, including antibacterial, anti-tartar or other active agents within the oral composition. Such anionic polycarboxylates are generally employed in the form of their free acids, or preferably partially neutralized or more preferably fully neutralized water soluble alkali metal (e.g., potassium and preferably sodium) or ammonium salts. The terms "synthetic" and "linear" exclude known thickening or gelling agents comprising carboxymethylcellulose and other derivatives of cellulose and natural gums, nor carbopols having reduced solubility due to cross-linkages.

Preferred copolymers are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. One preferable copolymer is methylvinylether/maleic anhydride. Examples of these copolymers are available from ISP Corporation under the trade name GANTREZ®, e.g., AN 139 (M.W. 1,100,000), AN 119 (M.W. 200,000); S-97 Pharmaceutical Grade (M.W. 1,500,000), AN 169 (M.W. 2,000,000), and AN 179 (M.W. 2,400,000); wherein the preferred copolymer is S-97 Pharmaceutical Grade (M.W. 1,500,000). In various embodiments where a synthetic anionic polycarboxylate is included in the oral composition, it is present in amounts of about 0.001 to about 5%, about 0.01 to about 4%, about 0.1 to about 3.5% or about 1 to about 3% of the oral care composition.

Additional optional oral care compounds that can be included in the oral composition include, for example, additional antibacterial agents, whitening agents, additional anticaries and tartar control agents not already discussed above, periodontal actives, abrasives, breath freshening agents, malodor control agents, tooth desensitizers, salivary stimulants and combinations thereof. Specifically, a non-limiting list of useful additional oral care compounds includes non-ionic antibacterial agents, including phenolic and bisphenolic compounds, such as, halogenated diphenyl ethers, including triclosan (2,4,4'-trichloro-2'-hydroxy-diphenylether, triclocarban (3,4,4-trichlorocarbanilide), as well as 2-phenoxyethanol, benzoate esters, and carbanilides. Useful anti-tartar agents include tin ion sources, such as such as stannous fluoride, stannous chloride, and stannous pyrophosphate, and/or zinc ion sources, such as zinc chloride, zinc citrate and zinc gluconate.

The oral compositions may be provided in an orally acceptable carrier or vehicle. The carrier can be a liquid, semi-solid, or solid phase, in the form of a mouth rinse, dentifrice (including toothpastes, toothpowders, and prophylaxis pastes), confectionaries (including lozenges, and gum), medicament, film, or any other form known to one of skill in the art. Selection of specific carrier components is dependent on the desired product form.

Conventional ingredients that can be used to form the carriers listed above are known to the skilled artisan. As recognized by one of skill in the art, the oral compositions optionally include other materials in addition to those components previously described, including for example, surface active agents, emulsifiers, and foam modulators, viscosity modifiers and thickeners, humectants, diluents, additional pH modifying agents, emollients, moisturizers, mouth feel agents, sweetening agents, flavor agents, colorants, preservatives, solvents, such as water and combinations thereof. Any given material may serve multiple purposes within two or more of such categories of materials. Preferably, such carrier materials are selected for compatibility and stability with all of the constituents of the active ingredient, including propolis extract and the one or more oral care active compounds selected for the oral composition.

Typical useful surface active agents are disclosed in the patent references referenced and discussed above, including in U.S. Pat. No. 4,894,220 and U.S. patent application Ser. No. 11/256,788. Surface active agents generally are an important aspect of the oral composition, as they can function as surfactants, emulsifiers foam modulators, and/or active ingredient dispersion agents. Thus, their selection for compatibility with the active ingredient constituents is important. For example, in embodiments where the oral composition has an active ingredient comprising a cationic antibacterial agent, it is preferred that the carrier comprises surfactants that are not strongly anionic, as such anionic compounds can bind to the cationic active ingredient potentially reducing its bioavailability.

Suitable surface active agents are those that are reasonably stable and foam throughout a wide pH range. These compounds are known in the art, and include non-soap anionic (e.g., sodium lauryl sulfate (SLS), N-myristoyl, and N-palmitoyl sarcosine), nonionic (e.g., Polysorbate 20 (polyoxyethylene 20 sorbitan monolaurate, TWEEN® 20) and Polysorbate 80 (polyoxyethylene 20 sorbitan mono-oleate, TWEEN® 80), Poloxamer 407, available under the trade name Pluronic® F127 from BASF Corporation), cationic, zwitterionic (e.g., cocoamidopropyl betaine and lauramido propyl betaine), and amphoteric organic synthetic detergents. In embodiments where the active ingredient comprises a cationic compound, the surface active agent may be chosen from: non-ionic surfactants, cationic surfactants, betaine surfactants, amphoteric surfactants or mixtures thereof. In various embodiments, one or more surface active agents are present in the oral composition in an amount of about 0.001% to about 5%, or about 0.5% to about 2.5%.

In embodiments where the oral composition is in the form of a mouthrinse, an exemplary carrier is substantially liquid. The term "mouthrinse" includes mouth washes, sprays, rinses, and the like. In such a preparation the orally acceptable carrier typically has an aqueous phase comprising either water, or a water and alcohol mixture. Further, in various embodiments, the oral carrier typically has a humectant, surfactant, and/or a pH buffering agent.

Depending on the extraction process and the concentration of the propolis extract used in the oral composition, it is possible that the smell and/or flavor of propolis extract is not aesthetically pleasing to some consumers. Thus it is desirable to formulate an oral composition that comprises components that reduce any adverse perception of the propolis extract. This can be accomplished by including relatively strong flavoring and/or sweetening agents into the oral composition. Further, in some embodiments, the flavoring agent may provide and/or enhance the flavors associated with bee products. Exemplary flavoring substances include those known to a skilled artisan, and are present in certain embodiments at a concentration of about 0.05% by weight to about 5% by weight.

In embodiments where an oral composition is in the form of a confectionary, an exemplary carrier is substantially solid or semi-solid. Confectionary carriers are known in the art. For a lozenge, the carrier typically comprises a lozenge base material (for example, comprising a non-cariogenic polyol and/or starch/sugar derivative), an emulsifier, a lubricant, a flavoring agent, a thickener, and optionally a coating material. Chewing gum carriers generally have a chewing gum base, one or more plasticizing agents, a sweetening agent, and a flavoring agent.

In embodiments where an oral composition is in the form of a film, an exemplary carrier is substantially solid or semi-solid. Generally, such film carriers comprise a water soluble or dispersible film forming agent, such as a hydrophilic polymer. Optionally, the film carrier may also comprise hydrophobic film forming polymers, either as a removable backing layer, or mixed with a hydrophilic film forming polymer. Film carriers optionally comprise additional ingredients such as plasticizers, surface active agents, fillers, bulking agents, and viscosity modifying agents.

In embodiments where an oral composition is in the form of a dentifrice, an exemplary carrier is substantially semi-solid or a solid. Dentifrices typically contain surface active agents, humectants, viscosity modifying agents and/or thickeners, abrasives, solvents, such as water, flavoring agents, and sweetening agents.

In certain embodiments, an oral composition is in the form of a medicament, such as a non-abrasive gel or ointment that can be applied to the gingival sulcus or margin and used in conjunction with wound dressings, gauze, films, and the like. Such gels may include both aqueous and non-aqueous gels. Aqueous gels generally comprise a polymer base, a thickener, a humectant, a flavoring agent, a sweetening agent, and a solvent, typically including water.

In various embodiments, an oral composition is provided within a single component or phase. In other embodiments, the oral composition includes both a first and a second component that are separately maintained. Maintaining the components separately requires only that the components are maintained in such a way as to substantially prevent the interaction of one component of the oral composition with another component of the oral composition. Typically, a dual component oral composition is employed where there are one or more incompatible ingredients included in the oral composition. For example, if the active ingredient comprises a second constituent that comprises a cationic antibacterial active, it is advantageous to maintain the cationic compound separately from strongly anionic components, such as anionic surface active ingredients. The separation of components can be accomplished through any means known in the art and includes chemical, physical, and mechanical means of separation or any combination of these. For example, the first and second components may be combined but certain components may be separately maintained by wrapping or encapsulating one or both in a film, coating, capsule, micelle, etc.

In various embodiments, a method promotes oral health in an oral cavity and treats plaque on an oral surface of a mammalian subject. In some embodiments, a method of providing one or more oral health benefits to an oral cavity of a mammalian subject comprises preparing an oral composition according to any of the various embodiments described above, where an active ingredient comprises a propolis extract, an oral care active compound and a source of fluoride ions. Various embodiments are directed to a method of preventing bacteria from forming a biofilm on an oral surface, a method of suppressing an immune system recognition of an antigen on an oral surface of a mammal, a method of reducing an immune system response, a method of suppressing production of one or more mediators of inflammation on an oral surface. In these embodiments, the prepared oral composition is contacted with an oral surface. The oral composition containing the active ingredient comprising a propolis extract may provide one or more oral health benefits, such as anti-gingivitis, anti-periodontitis, anti-caries, anti-tartar, anti-inflammatory, analgesic, anti-aging, and breath freshening.

Thus, any of the various embodiments of the oral care composition described above may be contacted with or applied regularly to an oral surface for at least once a day for a period of time. As used herein, "period of time" may refer to, for example, once a day, multiple days in a week, on a long-term daily or weekly basis, or even for the balance of a lifetime.

Various embodiments herein relate to methods of making oral compositions. As propolis extract is a natural product, it contains sensitive compounds that can be potentially denatured or damaged by heat treatment. Thus, certain embodiments are directed to methods of making an oral composition comprising admixing one or more carrier ingredients to form a homogenous mixture, and adding a propolis extract to the homogenous mixture at temperatures of less than about 40° C. to form the oral composition. In various embodiments the propolis extract may be added into the oral composition at ambient temperatures, e.g., less than about 30° C., or less than or equal to about 25° C.

The oral compositions may be prepared by suitably admixing the ingredients. For instance, in the preparation of a mouthrinse, the propolis extract may be dispersed in a flavor oil or an alcohol and then added to a mixture of humectants, surfactants, and water. The resulting rinse product is then packaged.

Dentifrices are typically prepared by adding various salts (including fluoride salts, when included in the composition), and sweeteners (e.g., saccharin), and any water-soluble oral care active ingredient compounds to water, where it is mixed. Into another container, all humectants, gums, and polymers may be added together. The water based mixture described above is added to the container with the humectants, gums, and polymers. The combined ingredients are optionally heated to a temperature of greater than about 40° C., for example from about 60° C. to about 70° C., to disperse the gums and polymers. The heated mixture is then cooled to less than approximately 38° C. (about 100° F.). The mixture is then combined with abrasives, where it is mixed at high speed under a vacuum for about 15 to about 20 minutes. The propolis extract is admixed into flavor oil (and/or alcohol), as are any lipophilic oral care active ingredients. This mixture is admixed to the water based mixture above, where it is mixed under high speed and vacuum until sufficiently dispersed. The surfactant(s) are added and the mixture is again mixed to disperse.

In certain embodiments, a method of making an oral composition comprises adding an additional oral care active ingredient to the one or more carrier ingredients prior to admixing. In other embodiments, an additional oral care active ingredient is added with the propolis extract to the homogenous mixture. Whether additional oral care active compounds are added to the one or more carrier ingredients prior to admixing them to form a homogenous mixture, or added to the mixture with the propolis extract after admixing, is dependent upon the nature of the additional active ingredient (for example, whether it can withstand heating to greater than or equal to about 40° C. and whether it is hydrophobic, hydrophilic, anionic, cationic, or non-ionic). One of skill in the art can readily determine the appropriate point in the method of making the oral composition to add the active ingredients, based upon these considerations. For example, in certain embodiments, where the additional constituent in the oral care active ingredient comprises a source of fluoride ions, the fluoride ion source can be added to the one or more carrier ingredients prior to the admixing because it is soluble in water.

The oral composition can be incorporated into confectionary and tropes. Such methods of forming confectionary (e.g., gum) or tropes (e.g., lozenges) are known by one of skill in the art, and can be prepared by, for example, stirring the propolis extract and other oral care active compound(s) into a warm gum base or coating the outer surface of a gum base (for example, jelutone, rubber latex, vinylite resins, inter alia), desirably with conventional plasticizers or softeners, sugar or other sweeteners or carbohydrates such as glucose, sorbitol and the like. In certain embodiments, the propolis extract is added to the gum base when it is at a temperature of less than or equal to about 40° C.

Where the oral composition is in the form of a film, it can be formed by any number of conventional film forming processes, such as conventional extrusion or solvent casting processes. For example, to prepare a film by solvent casting, a film forming polymer is dissolved in a sufficient amount of a solvent which is compatible with the polymer. After a solution has been formed, a plasticizer can be added with stirring, and heat can be applied if necessary to aid dissolution, until a clear and homogeneous solution has been formed, followed by the addition of the active ingredients, including propolis extract, surface active agents, bulking agents, and any other ingredients such as flavors and sweeteners at a temperature of, for example, less than about 40° C. For ease of use, the dry film can be cut into pieces of suitable size and shape and packed into a suitable container.

The oral compositions are applied to one or more oral surfaces in the oral cavity, and promote overall oral health, including inhibition of plaque formation, gingivitis, periodontitis, halitosis, and the like. In certain embodiments, the oral composition inhibits growth of various oral bacteria and further provides at least one of: anti-inflammatory activity, biofilm disruption and/or anti-attachment activity. Thus, certain oral compositions provide multiple oral care benefits simultaneously.

The present invention is further illustrated in the following non-limiting Example:

Example 1

A composition in accordance with the present invention was prepared, with the following constituents:

| Component | Weight % |
| --- | --- |
| Water | 40-70 |
| Sorbitol | 20-30 |
| Hydrated Silica | 10-20 |
| Methyl Vinyl Ether-Maleic | 1-3 |
| Acid Copolymer | |
| Sodium Lauryl Sulfate | 1-3 |
| Flavor | 0.5-3 |
| Titanium Dioxide | 0.1-3 |
| Carrageenan | 0.1-3 |
| NaOH | 0.1-3 |
| Sodium Salts (sulfate, carbonate, chloride) | 0.5-3 |
| Triclosan | 0.1-3 |
| Sweetener | 0.1-2 |
| Iron Oxide Hydrate | 0.001-1 |
| Propylene Glycol | 0.001-1 |
| Sodium Fluoride | 0.01-2 |
| Alcohol | 0.001-1 |
| Propolis Extract | 0.0001-3 |
| Color | 0.0001-1 |

The invention claimed is:

1. An encapsulated oral composition consisting essentially of:
a propolis extract; triclosan (2,4,4"-trichloro-2"-hydroxydiphenylether, triclocarban (3,4,4-trichlorocarbanilide); an anionic polymeric copolymer of methyl vinyl ether and maleic anhydride; and
a source of fluoride ions selected from the group consisting of sodium fluoride, stannous fluoride, monofluorophosphate and mixtures thereof.

* * * * *